US010271567B1

(12) United States Patent
Lu et al.

(10) Patent No.: US 10,271,567 B1
(45) Date of Patent: Apr. 30, 2019

(54) CHINESE MEAL PACKAGE AND PREPARATION METHOD THEREOF

(71) Applicant: Beijing DOCTOR LU Behavioral Medicine Science and Technology Research Institute Co., Ltd., Beijing (CN)

(72) Inventors: Mingfu Lu, Beijing (CN); Xiuping Zhang, Beijing (CN)

(73) Assignee: BEIJING DOCTOR LU BEHAVIORAL MEDICINE SCIENCE AND TECHNOLOGY RESEARCH INSTITUTE CO., LTD., Beijing (CN)

( * ) Notice: Subject to any disclaimer, the term of this patent is extended or adjusted under 35 U.S.C. 154(b) by 0 days.

(21) Appl. No.: 15/841,346

(22) Filed: Dec. 14, 2017

(30) Foreign Application Priority Data

Oct. 18, 2017 (CN) .................... 2017 1 09729468

(51) Int. Cl.
| | |
|---|---|
| A23L 3/00 | (2006.01) |
| A23L 29/00 | (2016.01) |
| A61K 36/8945 | (2006.01) |
| A61K 36/48 | (2006.01) |
| A61K 31/352 | (2006.01) |
| A61K 36/899 | (2006.01) |
| A61K 31/733 | (2006.01) |
| A61K 31/205 | (2006.01) |
| A61K 31/015 | (2006.01) |
| A61K 31/122 | (2006.01) |
| A61K 31/01 | (2006.01) |
| A61K 36/752 | (2006.01) |
| A61K 36/736 | (2006.01) |
| A61K 36/87 | (2006.01) |
| A61K 31/685 | (2006.01) |
| A61K 36/8994 | (2006.01) |
| A61K 36/185 | (2006.01) |
| A61K 36/738 | (2006.01) |
| A61K 31/51 | (2006.01) |
| A61K 31/525 | (2006.01) |
| A61K 31/675 | (2006.01) |
| A61K 31/714 | (2006.01) |
| A61K 31/375 | (2006.01) |
| A61K 31/07 | (2006.01) |
| A61K 31/592 | (2006.01) |
| A61K 31/593 | (2006.01) |
| A61K 31/355 | (2006.01) |
| A61K 31/4188 | (2006.01) |
| A61K 31/519 | (2006.01) |
| A61K 31/197 | (2006.01) |
| A61K 31/455 | (2006.01) |
| A61K 33/06 | (2006.01) |
| A61K 33/26 | (2006.01) |
| A61K 33/30 | (2006.01) |
| A61K 33/04 | (2006.01) |
| A61K 33/24 | (2019.01) |
| A61K 33/34 | (2006.01) |
| A61K 33/32 | (2006.01) |
| A23L 33/105 | (2016.01) |
| A23L 33/15 | (2016.01) |
| A23L 33/155 | (2016.01) |
| A23L 33/19 | (2016.01) |
| A23L 5/30 | (2016.01) |
| A61K 36/07 | (2006.01) |

(52) U.S. Cl.
CPC .................... *A23L 3/00* (2013.01); *A23L 5/34* (2016.08); *A23L 33/105* (2016.08); *A23L 33/15* (2016.08); *A23L 33/155* (2016.08); *A23L 33/19* (2016.08); *A61K 31/01* (2013.01); *A61K 31/015* (2013.01); *A61K 31/07* (2013.01); *A61K 31/122* (2013.01); *A61K 31/197* (2013.01); *A61K 31/205* (2013.01); *A61K 31/352* (2013.01); *A61K 31/355* (2013.01); *A61K 31/375* (2013.01); *A61K 31/4188* (2013.01); *A61K 31/455* (2013.01); *A61K 31/51* (2013.01); *A61K 31/519* (2013.01); *A61K 31/525* (2013.01); *A61K 31/592* (2013.01); *A61K 31/593* (2013.01); *A61K 31/675* (2013.01); *A61K 31/685* (2013.01); *A61K 31/714* (2013.01); *A61K 31/733* (2013.01); *A61K 33/04* (2013.01); *A61K 33/06* (2013.01); *A61K 33/24* (2013.01); *A61K 33/26* (2013.01); *A61K 33/30* (2013.01); *A61K 33/32* (2013.01); *A61K 33/34* (2013.01); *A61K 36/07* (2013.01); *A61K 36/185* (2013.01); *A61K 36/48* (2013.01); *A61K 36/736* (2013.01); *A61K 36/738* (2013.01); *A61K 36/752* (2013.01); *A61K 36/87* (2013.01); *A61K 36/899* (2013.01); *A61K 36/8945* (2013.01); *A61K 36/8994* (2013.01); *A23V 2002/00* (2013.01)

(58) Field of Classification Search
None
See application file for complete search history.

(56) References Cited

U.S. PATENT DOCUMENTS

2006/0088574 A1* 4/2006 Manning ................ A23L 33/40
424/439

* cited by examiner

*Primary Examiner* — Robert A Wax
*Assistant Examiner* — Melissa S Mercier
(74) *Attorney, Agent, or Firm* — Muncy, Geisler, Olds & Lowe, P.C.

(57) ABSTRACT

The disclosure discloses a Chinese meal package and a preparation method thereof. The Chinese meal package is prepared from the following raw materials in part by weight: a component A, a component B, a component C and a component D according to a ratio of 1 to 1 to 1 to 1.

9 Claims, 2 Drawing Sheets

CHINESE MEAL PACKAGE AND PREPARATION METHOD THEREOF

TECHNICAL FIELD OF THE INVENTION

The disclosure belongs to the technical field of health care products, and more particularly relates to a Chinese meal package and a preparation method thereof.

BACKGROUND ART

A meal package is a kind of food popular among people, and features rich nutrition and convenience in carrying and eating. At the present, there are lots of industrially purified deep sea fish oil products in the market, but these products have a potential hazard in the safety aspect. For example, some fishes, particularly shark and farmed trout, may be possibly polluted by mercury and other chemicals, thus leading to concentration of heavy metals during processing; in addition, for EPA and DHA, namely eicosapentaenoic acid and docosahexaenoic acid, their olefinic bonds, namely carbon-carbon double bonds, are of extremely instable chemical structures and are easy to oxidize, so that fish oil is low in storage property, and air, light and metal ions during processing may all lead to its oxygenolysis; and excessive fish oil supplementation would result in difficult coagulation of blood and increase a risk of haemorrhage. From the nutriology aspect, it is suggested to not take only one fatty acid, but to take all types of fatty acids. Taking deep sea fish oil as a health care product beyond a normal diet no doubt increases caloric intake in the diet of people, and is also unfavorable for a healthy dietary habit of a human body. Ultimately, uptake of sufficient ω-3 fatty acid through food is in greater accordance with a basic rule of human health.

Balanced dietary nutrition is a basis of health, which may provide various nutritional substances necessary to maintaining metabolic and physiological functions of the human body, and more importantly, may solve many health and safety problems caused by a modern dietary structure and a modern dietary habit.

It is an international popular trend to initiate a low energy diet which is also called a restricted energy diet and means that energy provided in a diet is lower than a normal demand. It aims to reduce body fat storage, lower the weight or reduce the organ energy metabolism burden and control states of illnesses.

The low energy diet is suitable for: patients in need of lowering the weight, such as a simple obesity; patients in need of reducing the organ energy metabolism burden to control the states of illnesses, such as a diabetes patient, a hypertension patient, a hyperlipidaemia patient and a coronary heart disease patient; and athletes in need of strict weight control.

1. To reduce total energy: according to calculation of a nutritionist, the energy intake of an adult per day is 2.09 to 4.18 MJ (500 to 1,000 kcal) less than that at ordinary times, and the decreased amount is based on the condition of the adult, but the total energy intake per day is not less than 3.34 to 4.18 MJ (800 to 1,000 kal) for the best to prevent ketoacidosis caused by extremely fast body fat mobilization. Staple food is prepared by blending coarse and fine grains for use.

2. To supply sufficient protein: as restricted energy supply lowers the intake of the staple food, the content of the protein in a diet is correspondingly increased, which at least accounts for 15 to 20 percent of the total energy, and high-quality protein should account for 50 percent or above to reduce decomposition of body tissues. Low-oil-content soybean products contain much protein, and fish, shrimps, marine food products and the like contain much protein and less fat, so that their calorie content is 80 to 60 percent less than that of pork.

3. To correspondingly reduce carbohydrates and fat: it is necessary to correspondingly reduce the supply amounts of the carbohydrates and the fat in the diet to reduce the supply of the total energy and guarantee the intake of the protein. The satiety is enhanced with a proper amount of fat, and it is better to control edible fat at 20 to 25 percent of the total calorie.

4. To make mineral substances and vitamins sufficient: reduction of food intake easily leads to insufficiency of the mineral substances such as iron and calcium and the vitamins such as vitamin B1, so that it is necessary to supplement the mineral substances and the vitamins with preparations.

5. To prevent a sense of hunger occurring in a patient as much as possible: the patient can eat dietary fiber-enriched vegetables and low-sugar fruits in the diet as many as possible.

In conclusion, low energy food is a developing direction of the international food industry nowadays. Different from traditional full energy food in the aspects of texture, flavor and taste, the low energy food is an important developing direction of the food industry in the 21st century, with a giant developing space and a wide market.

SUMMARY OF THE INVENTION

In view of the shortcomings in the prior art, the disclosure aims at providing a Chinese meal package and a preparation method thereof.

To achieve the above objective, the disclosure adopts technical schemes as follows:

A Chinese meal package is provided, characterized by being prepared from the following raw materials in part by weight:

a component A, a component B, a component C and a component D according to a ratio of 1 to 1 to 1 to 1, wherein the component A is prepared from the following raw material components:

3,000 to 3,500 parts of an agaricus blazei extract
60,000 to 65,000 parts of yam
3,000 to 3,500 parts of phaseolus calcaratus
200 to 240 parts of glabridin
5,000 to 5,500 parts of a black bean peel extract
the component B is prepared from the following raw material components:
2,000 to 2,200 parts of total sugar
2,122.3 to 2,431.6 parts of mineral substances
20,000 to 25,000 parts of corn fiber powder
17,000 to 20,000 parts of inulin
60,000 to 65,000 parts of soybean isolate protein powder
500 to 520 parts of L-carnitine
200 to 220 parts of β carotene
100 to 120 parts of Q10 coenzyme
3,000 to 3,300 parts of lycopene
500 to 530 parts of a citrus extract
6,000 to 6,300 parts of a conifer cherry extract
600 to 650 parts of a grape seed extract
10,000 to 15,000 parts of lecithin
4,000 to 4,300 parts of a tremella extract
2,000 to 2,200 parts of a white hyacinth bean extract
4,000 to 4,300 parts of a semen coicis extract 2,000 to 2,300 parts of an okra extract
2,000 to 2,200 parts of a rose flower extract
the component C is prepared from the following raw material components:
32 to 38 parts of vitamin B1
32 to 41 parts of vitamin B2
32 to 45 parts of vitamin B6
0.032 to 0.02 parts of vitamin B12
360 to 400 parts of vitamin C
0.72 to 1 part of vitamin A
0.022 to 0.5 part of vitamin K
0.009 to 0.056 part of vitamin D
420 to 450 parts of vitamin E
0.032 to 0.56 parts of biotin
0.48 to 1 part of folic acid
32 to 55 parts of pantothenic acid
32 to 50 parts of nicotinic acid
the component D is prepared from the following raw material components:
550 to 650 parts of milk
80,000 to 90,000 parts of deionized water.
Wherein the mineral substances consist of the following raw material components in part by weight: 1,300 to 1,500 parts of calcium, 650 to 720 parts of magnesium, 21.6 to 35 parts of iron, 144 to 165 parts of zinc, 0.3 to 1 part of selenium, 0.3 to 0.9 part of chromium, 1.8 to 2.8 parts of copper, 3.6 to 5.6 parts of manganese and 0.7 to 1.3 parts of vanadium.
Wherein the total sugar is prepared from one of or a combination of several of sorbitol, xylooligosaccharide and sucralose.
Wherein the raw material components of the meal package and the weight parts are as follows:
the component A is prepared from the following raw material components:
3,000 parts of the agaricus blazei extract
60,000 parts of the yam
3,000 parts of the phaseolus calcaratus
200 parts of the glabridin
5,000 parts of the black bean peel extract
the component B is prepared from the following raw material components:
2,000 parts of the total sugar
1,300 parts of calcium
650 parts of magnesium
21.6 parts of iron
144 parts of zinc
0.3 part of selenium
0.3 part of chromium
1.8 parts of copper
3.6 parts of manganese
0.7 part of vanadium
20,000 parts of the corn fiber powder
17,000 parts of the inulin
60,000 parts of the soybean isolate protein powder
500 parts of the L-carnitine
200 parts of the β carotene
100 parts of the Q10 coenzyme
3,000 parts of the lycopene
500 parts of the citrus extract
6,000 parts of the conifer cherry extract
600 parts of the grape seed extract
10,000 parts of the lecithin
4,000 parts of the tremella extract
2,000 parts of the white hyacinth bean extract
4,000 parts of the semen coicis extract 2,000 parts of the okra extract
2,000 parts of the rose flower extract
the component C is prepared from the following raw material components:
32 parts of the vitamin B1
32 parts of the vitamin B2
32 parts of the vitamin B6
0.032 parts of the vitamin B12
360 parts of the vitamin C
0.72 part of the vitamin A
0.022 part of the vitamin K
0.009 part of the vitamin D
420 parts of the vitamin E
0.032 parts of the biotin
0.48 part of the folic acid
32 part of the pantothenic acid
32 part of the nicotinic acid
the component D is prepared from the following raw material components:
550 parts of the milk
80,000 parts of the deionized water.
Wherein the raw material components of the meal package and the weight parts are as follows:
the component A is prepared from the following raw material components:
3,500 parts of the agaricus blazei extract
65,000 parts of the yam
3,500 parts of the phaseolus calcaratus
240 parts of the glabridin
5,500 parts of the black bean peel extract
the component B is prepared from the following raw material components:
2,200 parts of the total sugar
2,431.6 parts of the mineral substances
25,000 parts of the corn fiber powder
20,000 parts of the inulin
65,000 parts of the soybean isolate protein powder
520 parts of the L-carnitine
220 parts of the β carotene
120 parts of the Q10 coenzyme
3,300 parts of the lycopene
530 parts of the citrus extract
6,300 parts of the conifer cherry extract
650 parts of the grape seed extract
15,000 parts of the lecithin
4,300 parts of the tremella extract
2,200 parts of the white hyacinth bean extract
4,300 parts of the semen coicis extract
2,300 parts of the okra extract
2,200 parts of the rose flower extract
the component C is prepared from the following raw material components:
38 parts of the vitamin B1
41 parts of the vitamin B2
45 parts of the vitamin B6
0.02 parts of the vitamin B12
400 parts of the vitamin C
1 part of the vitamin A
0.5 part of the vitamin K
0.056 part of the vitamin D
450 parts of the vitamin E
0.56 parts of the biotin
1 part of the folic acid
55 part of the pantothenic acid
50 part of the nicotinic acid the component D is prepared from the following raw material components:
650 parts of the milk
90,000 parts of the deionized water;
wherein the mineral substances consist of the following raw material components in part by weight: 1,500 parts of calcium, 720 parts of magnesium, 35 parts of iron, 165 parts of zinc, 1 part of selenium, 0.9 part of chromium, 2.8 parts of copper, 5.6 parts of manganese and 1.3 parts of vanadium.

Wherein the meal package provides energy of 800 to 850 Kcal/day/person, and 90 to 95 percent of high-quality protein.

A preparation method of a Chinese meal package is provided, including:
Step I, pretreatment of raw materials;
Step II, drying;
Step III, freeze grinding;
Step IV, filtering with a biological ceramic film;
Step V, infrared-microwave drying;
Step VI, packaging and sterilizing a finished product.

Wherein the step I of pretreatment of the raw materials specifically includes: Step (1) weighing the raw material components according to ratios, cleaning a component A to remove impurities, sterilizing the component A in a far infrared sterilizer for 20 to 25 seconds, then performing high temperature sterilization under the set conditions of a sterilization temperature range between 80 and 90 DEG C., a pressure between 8 and 10 MPa and a sterilization time length range between 8 and 13 minutes;

Step (2) soaking the sterilized component A in milk for 1 to 24 hours till the milk content is 20 to 25 weight percent;
the step II of drying specifically includes:
Step (3) drying the milk-soaked component A in a vacuum microwave dryer at a drying temperature of 30 to 35 DEG C. for 5 to 8 minutes, and controlling the vacuum degree at 5 to 8 KPa and the microwave power at 200 to 400 W, thus obtaining a dried component A;

Step (4) freezing the component A dried in the step (3) at −15 to −20 DEG C. for 2 to 4 hours for freezing treatment, then taking out the component A, putting the component A into a vacuum freeze dryer, firstly freezing the component A at a cooling speed of 5 to 10 DEG C./min till the temperature of the component A is −25 to −35 DEG C., maintaining the temperature for 2 to 4 hours, then putting the component A into a freezer at a temperature of −25 to −30 DEG C. for constant temperature freezing for 3 hours, thus obtaining a freeze-dried component A; the step III of freeze grinding specifically includes:

Step (5) grinding the freeze-dried component A in an ultrafine cell wall breaking grinder into powder of 400 meshes, adding deionized water in an amount twice that of the component A powder into the ground component A powder, and then treating the component A powder with an ultrasonic continuous flow cell crushing machine at an ultrasonic frequency of 15 to 30 KHz, power of 1,000 to 1,500 W and the flow of suspension per hour of 10 Kg, thus obtaining crushed component A powder suspension for later use;

the step IV of filtering with the biological ceramic film specifically includes:
Step (6) filtering the component A powder suspension: filtering the component A powder suspension with the microfiltration biological ceramic film, respectively collecting interceptions and filtrate, and then continuously filtering the filtrate with an ultrafiltration film, thus obtaining ultrafiltration film filtrate A for later use, wherein the microfiltration film is an alumina-based nano inorganic film with a molecular weight cut-off of 1,000 MW and the microfiltration temperature is 30 to 35 DEG C.; the ultrafiltration film has a molecular weight cut-off of 300 MW and the ultrafiltration temperature is 40 DEG C.; the nano inorganic film has a thickness of 10 to 15 microns, and is prepared from the following raw materials in part by weight: 15 to 20 parts of silicon nitride, 1 to 5 parts of zinc oxide, 2 to 3 parts of yttria stabilized zirconia, 10 to 15 parts of titanium carbide, 5 to 8 parts of glass fiber, 3 to 5 parts of aluminum oxide and 1 to 3 parts of magnesium oxide;

Step (7) concentrating the material solution A by a vacuum adsorption method at a vacuum adsorption concentration temperature of 30 to 40 DEG C. for 2 to 4 hours, wherein an adsorbent for vacuum adsorption concentration is active carbon or nonpolar macroporous resin, which is 1 to 2 times the weight of the original component A, and then obtaining a concentrated solution A;

the step V of infrared-microwave drying includes:
Step (8) performing hot air-infrared-microwave drying on the obtained concentrated solution A in a drying cavity, wherein the hot air temperature is 40 to 45 DEG C., the far infrared radiation intensity is 0.5 to 0.8 W/cm<2>, the power in the first stage of microwave heating is 300 to 400 W, the power in the second stage is 400 to 500 W, and the power in the third stage is 500 to 400 W, the speed of a conveying belt is 5 to 10 m/min, and the drying operation is cyclically performed for 3 to 4 times; and drying the concentrated solution A under an infrared and microwave environment till the moisture content is less than 4 percent, thus obtaining a component A dry powder;

the step VI of packaging and sterilizing a finished product:
Step (9) adding the obtained component A dry powder, a component B, a component C and a residual component D into a stirrer according to raw material ratios for raw material mixing, stirring the materials in the stirrer at a rotating speed of 1,500 r/min for 25 to 35 minutes, then stopping the stirrer, homogenizing the raw materials, controlling the temperature of the material solution at 40 to 50 DEG C. and the homogenization pressure at 10 to 15 MPa during homogenization, performing metering and bagging, and performing pasteurization for 10 to 15 minutes, thus obtaining a finished product.

Wherein soybean processing includes: selecting sun-cured and full high-quality soybeans which have a golden yellow color and are free of pest damage, washing the soybeans with water, weighing the soybeans according to a raw weight of the amount, frying the soybeans in a pan till the soybeans are cooked, and grinding the soybeans into powder of 200 meshes; soybeans for the soybean isolate protein powder are processed by: baking the soybeans at 80 to 100 DEG C. for 20 to 30 minutes, soaking the soybeans into a $NaHCO_3$ solution with the mass percent concentration of 2 to 3 percent for 120 to 150 seconds, quickly freezing the soybeans at −20 DEG C. for 5 to 10 minutes, and drying the soybeans at 50 to 60 DEG C. with hot air for 110 to 150 minutes.

Spirulina powder: it contains rich protein, amino acids, vitamins, mineral substances, seaweed polysaccharide, phycocyanobilin, B-carotene, chlorophyll, linolenic acid and other nutritional active substances.

Mineral substances: like the vitamins, mineral substances are elements necessary to a human body, which cannot be self-produced and synthesized, and insufficiency of the mineral substances in a human body may lead to many symptoms.

Composite vitamins: vitamins are essential substances in the human body, and although the demand quantity for the vitamins is small, the vitamins must be supplemented via uptake as they cannot be synthesized in the body. The vitamins are crucial for maintaining normal growth and development of the human body and regulating various physiological functions.

Sucralose: it is an intense sweetener. The sucralose is a non-nutritional sweetener featuring low calorie, high sweetness and edible safety, which would neither cause increase of blood glucose nor lead to fluctuation of the blood glucose after being eaten, so that the sucralose is suitable for patients suffering from obesity, cardiovascular diseases, diabetes and the like.

Corn: it contains 2.9 percent of cellulose, 4 percent of protein, 1.2 percent of fat, 22.8 percent of carbohydrates as well as mineral substance elements, vitamins and the like, and the digestion rate is 90 percent or above. The corn is rich in vitamin B6, nicotinic acid, vitamin C, vitamin E, isomaltose oligosaccharide and the like, and has effects of dredging intestines and stomach, prolonging life, maintaining beauty, regulating middle energizer, stimulating appetite, reducing blood fat and reducing cholesterol. Lutein and zeaxanthin in the corn may resist aging of eyes.

Soybean: its protein content is twice more than that of pork and 2.5 times that of egg. The soybean has effects of tonifying qi, moisturizing skin, moistening spleen, removing accumulation dysentery, loosening the center, descending qi, promoting defecation, eliminating edema and treating pyogenic infections. The soybean digestion and absorption rate is 65 percent, and the soybean contains high-quality protein and fatty acids (not including cholesterol) necessary to the human body and is enriched with phospholipid and various vitamins and trace elements such as VA, VE and VB families, iron, zinc, calcium, phosphorus and potassium. These substances have medical health care effects of dissolving thrombus, preventing cardiovascular and cerebrovascular diseases, preventing senile dementia, preventing constipation, resisting oxidization, killing bacteria, maintaining beauty, reducing weight and reducing blood pressure, and are increasingly and widely recognized.

Blueberry: with rich anthocyanin, it has effects of activating retinas, improving the eyesight and preventing fatigue of eyeballs, contains a large amount of vitamins, acids, SOD, arbutin, protein, anthocyanin and edible fiber, and has functions of preventing aging of cranial nerves, strengthening heart, resisting cancers, softening blood vessels, enhancing human organ immunity and the like.

Radix puerariae: it has effects of resolving flesh, bringing down a fever, promoting eruption, promoting the production of body fluid to relieve thirst, invigorating splenic yang, checking diarrhea and the like.

The health care meal package is a part of an anti-cancer scheme. The anti-cancer scheme is an intervention plan based on a way of life, specifically including: Nutrient enrichment: 3 to 5 meal packages of the disclosure are eaten per day, and each package is 25 grams in weight.

Moderate exercise: 15-minute quick walking or other aerobic exercises are done twice a day to achieve effects of generating heat on the back and sweats on the forehead.

The radix puerariae is a dried root of pueraria lobata belonging to a leguminous plant, and is regularly called pueraria lobata. It is excavated and picked in autumn and winter, and is cut into thick slices or small blocks for drying while it is fresh. The radix puerariae internally contains 12 parts of flavonoids compounds such as puerarin, soybean flavonoid glycoside, anthocyanin and other nutritients, and further contains protein, amino acids, sugar and mineral substances such as iron, calcium, copper and selenium which are necessary to the human body, so that the radix puerariae is a noble nourishment suitable for people of all ages, and has a good reputation of "Thousand Year Ginseng". The radix puerariae has a medicinal value and nutrition and health care effects, and is mainly produced in Hubei, Guizhou, Guangxi, Jiangsu, Jiangxi, Hu'nan and the like.

Effects and actions of the radix puerariae are as follows:

All portions on the radix puerariae are valuable. There is a long history of application of the radix puerariae in China, and even there are application ways for kudzu vines, kuzunoha and pueraria flowers. According to records in the *Compendium of Materia Medica*: radix puerariae is cool in nature and mild in property and tastes sweet, and has effects of clearing away heat, decreasing internal heat and expelling toxins. Further analysis with a modern medical method shows that the radix puerariae is enriched with 13 isoflavones substances, including puerarin, miroestrol, puerarin xyloside, daidzein and the like.

The radix puerariae has effects of: invigorating splenic yang, resolving flesh, promoting eruption, checking diarrhea, relieving restlessness and quenching thirst. It may treat typhoid fever, warm headache, feverish dysphoria, consumptive thirst, diarrhoea, dysentery, slow toxic ecchymosis, hypertension, stenocardia, deafness and the like.

It has a treating effect on hypertension, hyperlipidemia, hyperglycemia and cardiovascular and cerebrovascular diseases.

Total flavonoids of the radix puerariae may obviously increase cerebral blood flow and increase blood flow in a coronary artery. The puerarin may slow down the heart beat, enhance the myocardial contractility and lower aortic pressure. The total flavonoids, the daidzein and the puerarin of the radix puerariae achieve an obvious treating effect on headache, dizziness, tinnitus and other symptoms which are caused by hypertension. Effective components, such as the daidzein, the daidzin and the miroestrol, in the radix puerariae have an inhibition effect on cell multiplication of hormone-dependent tumors such as the breast cancer, the uterine veil cancer, the ovarian cancer, the colorectal cancer and the prostatic cancer. The puerarin may reduce blood glucose and obviously reduce serum cholesterol.

The immunological function is enhanced:

The rich flavonoids compounds in the radix puerariae may effectively clear away free radicals and inhibit erythrocyte membranes and oxidative damage to a liver, a spleen and brain tissues. Pueraria flavone is used for preventing oxidative damage to biological membranes, and the radix puerariae may enhance the carbon particle uptake functions of the liver and the spleen and also recovery cellular immune responses. If people often eat the radix puerariae, effects of regulating functions of a human body, enhancing the physique, improving the organ disease resistance, resisting aging, prolonging life and maintaining youthful vigor forever would be achieved.

Rhizoma polygonati is mostly used for treating weakness of the spleen and the stomach, lung-dryness due to deficiency of yin, fatigueness, thirst, reduced appetite, dry cough due to deficiency of the lung, insufficiency of blood and essence, dry cough with little phlegm, premature graying of hairs, insufficiency of blood and essence, internal heat type consumptive thirst and the like, and has an outstanding treating effect on diabetes;

Mulberries are cold in nature and taste sweet, and have effects of tonifying the liver, benefiting the kidney, promoting the secretion of saliva or body fluid, moistening dryness, blackening hairs, improving eyesight and the like; peanut coats contain rich nutritional components, and may tonify qi of the spleen and the stomach; according to the western medicine, the peanut red skins may inhibit dissolving of fibrous protein, increase the content of blood platelets, improve the quality of the blood platelets, improving defects of blood coagulation factors, enhance the contraction function of blood capillaries and promote the bone marrow hematopoietic function; and sea salt contains richer calcium, magnesium, potassium and sulfur and trace elements such as iron and zinc, may effectively improve the taste of a rhizoma polygonati energy meal. The various above-mentioned black food materials and medicinal materials are scientifically proportioned to prepare powder, and the powder has the advantages of simplicity and convenience in preparation and taking, replaceability for breakfast, warm benefiting, favorability for absorption, safety and effectiveness, and has a good dietary treating effect on graying and dryness of hairs due to deficiency of the kidney; and in addition, by soaking in selenium-enriched water, the rhizoma polygonati energy meal is enriched with selenium and enhances the health care effect.

The white hyacinth bean extract in the disclosure is prepared by the following method: cleaning white hyacinth beans, removing impurities, performing sterilization in an far infrared sterilizer for 60 to 80 seconds, then performing high temperature sterilization, and setting a sterilization temperature range at 100 to 110 DEG C., a pressure at 2 to 4 MPa and a sterilization time length range at 30 to 40 minutes; soaking the white hyacinth beans in water for 40 to 50 hours till the moisture content reaches 20 to 25 percent; adding the white hyacinth beans subjected to vacuum drying into a stirring ball grinder for grinding at a rotating speed of 300 to 500 r/min for 3 to 5 minutes, thus obtaining white hyacinth bean powder, and grinding the powder in an ultrafine cell wall breaking grinder till the powder is of 200 meshes or above; adding ethanol, which is 1.1 to 1.5 times the weight of the white hyacinth bean powder and has the concentration of 40 to 50 percent, into the ground white hyacinth bean powder, performing treatment in an ultrasonic continuous flow cell crusher at an ultrasonic frequency of 15 to 40 KHz, power of 1,000 to 3,000 W and flow of suspension per hour of 15 Kg, thus obtaining crushed white hyacinth bean powder suspension; adding the white hyacinth bean powder suspension into a distillation retort, then adding cellulase, which is 0.6 to 0.8 percent of the weight of the white hyacinth bean powder suspension, and water for soaking at normal temperature for 4 to 6 hours, thus obtaining an extracting solution; feeding water vapor from the bottom of the distillation retort to heat the extracting solution, and after the extracting solution is boiled, performing extraction for 2 to 3 hours, thus obtaining mixed steam; condensing the obtained mixed steam through a condenser, thus obtaining an oil-water mixture; performing oil-water separation on the oil-water mixture, which is obtained by condensation, through an oil-water separator, thus obtaining coarse white hyacinth bean oil and water;

injecting the obtained coarse white hyacinth bean oil into an extraction device by using a feeding device, closing a valve on the feeding device, and vacuumizing the extraction device; adding an extractant into the extraction device for repeated extraction at a temperature of 30 to 50 DEG C. and a pressure of 1 to 2 MPa for 2 hours; transferring an obtained extracting liquid into an evaporation device to separate and purify a solvent and an extract, wherein for the extraction, supercritical extraction is performed by taking supercritical $CO_2$ fluid as the extractantextractant and ethanol with the volume concentration of 30 to 45 percent as an entrainer, an extract is obtained via separation through a separation kettle, the extraction temperature is 25 to 38 DEG C., the extraction pressure is 15 to 22 MPa, the extraction time is 1.5 to 3 hours, a ratio of the mass Kg of the raw material to the volume L of an extraction kettle is (0.2 to 0.5) to 1, and a ratio of the use amount L of the entrainer to the volume L of the extraction kettle is (0.05-0.07) to 1; after the primary extraction is completed, pressing a material solution into the evaporation device, adding the extractant into the extraction device again, then transferring the material solution in the evaporation device into the extraction device for secondary extraction, wherein the extraction is performed for at least six times; and putting the extract obtained via extraction into a molecular distiller, performing molecular distillation under conditions of 5 to 10 Pa and 160 to 180 DEG C., and collecting obtained corresponding plant essential oil; after the essential oil is layered, and separating out the upper layer which is white hyacinth bean essential oil, wherein the oil yield of the white hyacinth bean essential oil is 15 to 20 percent, and the purity of the white hyacinth bean essential oil is up to 98 percent or above.

Wherein the component C further contains 175 to 365 parts of deep sea fish oil which is selected from one of or a combination of several of trout, thon, mackerel, tuna, garrupa, dorado, catfish and gadus.

Beneficial Effects

A few of people suffer from slow fecal transit, which is mainly caused by little food intake and small excrement size, so that those people may not defecate in the previous few days. Cellulose is added to enlarge the excrement size, and accumulated excrements may be cleared away more thoroughly. Tremella is added to moisten the lung and relax the bowels. Xylooligosaccharide is added to accelerate regulation of intestinal flora.

A few of people look off color, which is mainly because fat burning in the nursing period increases the metabolic burden and some organ functions may not follow the nursing requirements. For yellow face, semen coicis, yam and white hyacinth beans are added to enhance spleen regulation. For brown face, okras are added to tonify the kidney. Skin-whitening roseberries and glabridin from liquorice are further added.

The main process of the disclosure is a physical processing method, which is favorable for safety control over a food processing process, thus improving the quality and the safety of a product.

The disclosure saves energy, reduces consumption, lowers equipment loss and prolongs the aging time. Compared with a conventional method, the method has the advantages that the aging time of equipment is prolonged by 50 percent, so that the labor intensity of a worker is substantially reduced, and the labor productivity is substantially improved;

the disclosure combines mineral substances or composite vitamins, and lots of researches show that in the process of manufacturing a meal package, all raw materials are effectively coordinated according to a four-component method to fully exert their synergistic effect; and according to the preparation technology provided by the disclosure, the mineral substances or the composite vitamins which are added and supplemented conform to a proportional quantity in accordance with a demand of a human body, thus achieving the best state. Compared with a conventional meal package the meal package provided by the disclosure has the advantages that the vitamin absorption rate of an eater is increased by 80 percent, the mineral substance absorption rate is increased by 70 percent, and a balanced state of nutrition is improved.

Figure 1:
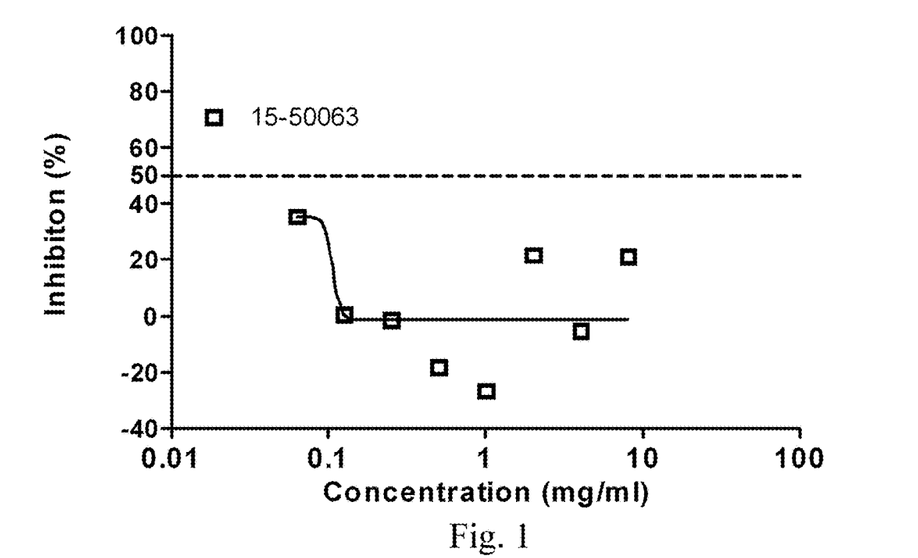
FIG. 1 shows the impact of ganoderma broken-down wall spore powder on AGS cell inhibition.
Figure 2:
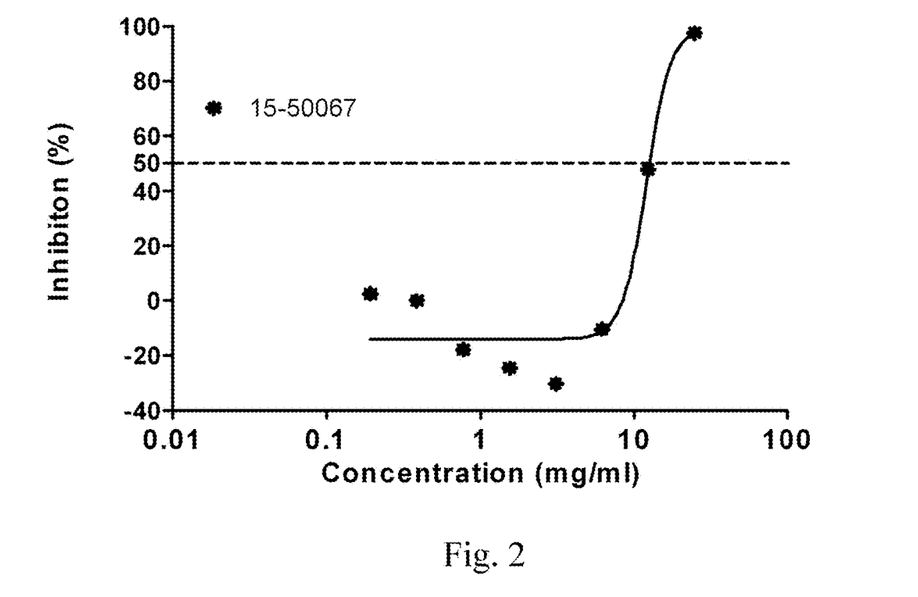
FIG. 2 shows the impact of an experience meal package on AGS cell inhibition.
Figure 3:
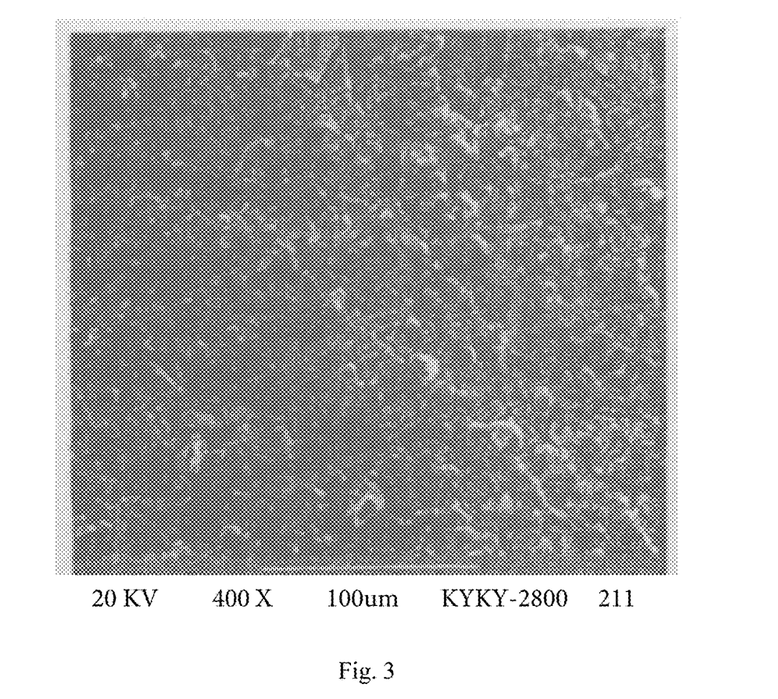
FIG. 3 shows an SEM graph of a nano inorganic film.
Figure 4:
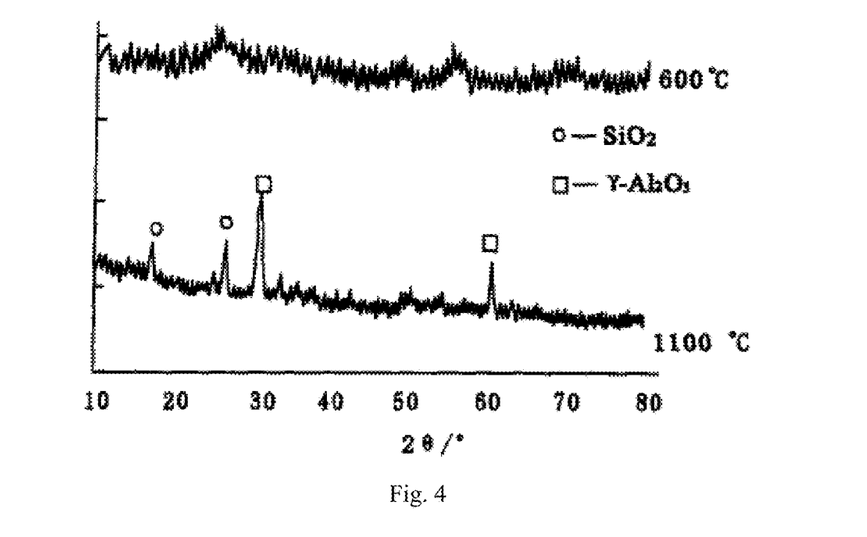
FIG. 4 shows an XRD graph of a composite film obtained by calcining of a nano inorganic film at 600 DEG C. and 1,100 DEG C. of an embodiment 4.

Comparison of the effect (FIG. 2) of the meal package with the effect (FIG. 1) of a conventional spore powder raw material in this field shows that the inhibiting effects of ganoderma broken-down wall spore powder with different concentrations on gastric cancer cells all reach 50 percent, and the inhibiting effects of the concentrations on the gastric cancer cells neither have an obvious changing trend. Thus, the ganoderma broken-down wall spore powder has no obvious effect on the gastric cancer cells. When the concentration of an experience meal package is higher than 12 mg/ml, with increase of the concentration, the inhibiting effect on growth of the gastric cancer cells is in a linear increase trend, and the maximum inhibiting rate is almost 100 percent. Thus, the experience meal package with the concentration higher than 12 mg/ml has the inhibiting effect on the gastric cancer cells, and with the increase of the concentration, the inhibiting effect on the cells is enhanced.

DETAILED DESCRIPTION OF THE INVENTION

Embodiment 1

Raw material components of a meal package and the weight parts are as follows:

a component A is prepared from the following raw material components:
   3,000 parts of the agaricus blazei extract
   60,000 parts of the yam
   3,000 parts of the phaseolus calcaratus
   200 parts of the glabridin
   5,000 parts of the black bean peel extract a component B is prepared from the following raw material components:
   2,000 parts of the total sugar
   1,300 parts of calcium
   650 parts of magnesium
   21.6 parts of iron
   144 parts of zinc
   0.3 part of selenium
   0.3 part of chromium
   1.8 parts of copper
   3.6 parts of manganese
   0.7 part of vanadium
   20,000 parts of the corn fiber powder
   17,000 parts of the inulin
   60,000 parts of the soybean isolate protein powder
   500 parts of the L-carnitine
   200 parts of the β carotene
   100 parts of the Q10 coenzyme
   3,000 parts of the lycopene
   500 parts of the citrus extract
   6,000 parts of the conifer cherry extract
   600 parts of the grape seed extract
   10,000 parts of the lecithin
   4,000 parts of the tremella extract
   2,000 parts of the white hyacinth bean extract
   4,000 parts of the semen coicis extract
   2,000 parts of the okra extract
   2,000 parts of the rose flower extract a component C is prepared from the following raw material components:
   32 parts of the vitamin B1
   32 parts of the vitamin B2
   32 parts of the vitamin B6
   0.032 parts of the vitamin B12
   360 parts of the vitamin C
   0.72 part of the vitamin A
   0.022 part of the vitamin K
   0.009 part of the vitamin D
   420 parts of the vitamin E
   0.032 parts of the biotin
   0.48 part of the folic acid
   32 part of the pantothenic acid
   32 part of the nicotinic acid a component D is prepared from the following raw material components:
   550 parts of the milk
   80,000 parts of the deionized water.

The total sugar is prepared from one of or a combination of several of sorbitol, xylooligosaccharide and sucralose.

Embodiment 2

Raw material components of a meal package and the weight parts are as follows:

a component A is prepared from the following raw material components:
   3,500 parts of the agaricus blazei extract
   65,000 parts of the yam
   3,500 parts of the phaseolus calcaratus
   240 parts of the glabridin
   5,500 parts of the black bean peel extract a component B is prepared from the following raw material components:
   2,200 parts of the total sugar
   2,431.6 parts of the mineral substances
   25,000 parts of the corn fiber powder
   20,000 parts of the inulin
   65,000 parts of the soybean isolate protein powder
   520 parts of the L-carnitine
   220 parts of the β carotene
   120 parts of the Q10 coenzyme
   3,300 parts of the lycopene
   530 parts of the citrus extract
   6,300 parts of the conifer cherry extract
   650 parts of the grape seed extract
   15,000 parts of the lecithin
   4,300 parts of the tremella extract
   2,200 parts of the white hyacinth bean extract
   4,300 parts of the semen coicis extract
   2,300 parts of the okra extract
   2,200 parts of the rose flower extract a component C is prepared from the following raw material components:
   38 parts of the vitamin B1
   41 parts of the vitamin B2
   45 parts of the vitamin B6
   0.02 parts of the vitamin B12
   400 parts of the vitamin C 1 part of the vitamin A
0.5 part of the vitamin K
0.056 part of the vitamin D
450 parts of the vitamin E
0.56 parts of the biotin
1 part of the folic acid
55 part of the pantothenic acid
50 part of the nicotinic acid
a component D is prepared from the following raw material components:
650 parts of the milk
90,000 parts of the deionized water;
wherein the mineral substances consist of the following raw material components in part by weight: 1,500 parts of calcium, 720 parts of magnesium, 35 parts of iron, 165 parts of zinc, 1 part of selenium, 0.9 part of chromium, 2.8 parts of copper, 5.6 parts of manganese and 1.3 parts of vanadium.

Wherein the meal package provides the energy of 800 Kcal/day/person, and 90 percent of high-quality protein.

The total sugar is prepared from one of or a combination of several of sorbitol, xylooligosaccharide and sucralose.

Embodiment 3

A preparation method of a Chinese meal package is provided, including:
Step I, pretreatment of raw materials;
Step II, drying;
Step III, freeze grinding;
Step IV, filtering through a biological ceramic film;
Step V, infrared-microwave drying;
Step VI, packaging and sterilizing a finished product.

Wherein the step I of pretreatment of the raw materials specifically includes:
Step (1) weighing the raw material components according to ratios, cleaning a component A to remove impurities, sterilizing the component A in a far infrared sterilizer for 20 seconds, then performing high temperature sterilization under the set conditions of a sterilization temperature range of 80 DEG C., a pressure of 8 MPa and a sterilization time length range of 8 minutes;

Step (2) soaking the sterilized component A in milk for 1 hour till the milk content is 20 weight percent;

the step II of drying specifically includes:
Step (3) drying the milk-soaked component A in a vacuum microwave dryer at a drying temperature of 30 DEG C. for 5 minutes, and controlling the vacuum degree at 5 KPa and the microwave power at 200 W, thus obtaining a dried component A;

Step (4) freezing the component A dried in the step (3) at −15 DEG C. for 2 hours for freezing treatment, then taking out the component A, putting the component A into a vacuum freeze dryer, firstly freezing the component A at a cooling speed of 5 DEG C./min till the temperature of the component A is −25 DEG C., maintaining the temperature for 2 hours, then putting the component A into a freezer at a temperature of −25 DEG C. for constant temperature freezing for 3 hours, thus obtaining a freeze-dried component A;

the step III of freeze grinding specifically includes:
Step (5) grinding the freeze-dried component A in an ultrafine cell wall breaking grinder into powder of 400 meshes, adding deionized water in an amount twice that of the component A powder into the ground component A powder, and then treating the component A powder with an ultrasonic continuous flow cell crushing machine at an ultrasonic frequency of 15 KHz, power of 1,000 W and the flow of suspension per hour of 10 Kg, thus obtaining crushed component A powder suspension for later use;

the step IV of filtering with the biological ceramic film specifically includes:
Step (6) filtering the component A powder suspension: filtering the component A powder suspension with the microfiltration biological ceramic film, respectively collecting interceptions and filtrate, and then continuously filtering the filtrate with an ultrafiltration film, thus obtaining ultrafiltration film filtrate A for later use, wherein the microfiltration film is an alumina-based nano inorganic film with a molecular weight cut-off of 1,000 MW and the microfiltration temperature is 30 DEG C.; the ultrafiltration film has a molecular weight cut-off of 300 MW and the ultrafiltration temperature is 40 DEG C.; the nano inorganic film has a thickness of 10 microns, and is prepared from the following raw materials in part by weight: 15 parts of silicon nitride, 1 part of zinc oxide, 2 parts of yttria stabilized zirconia, 10 parts of titanium carbide, 5 parts of glass fiber, 3 parts of aluminum oxide and 1 part of magnesium oxide;

Step (7) concentrating the material solution A by a vacuum adsorption method at a vacuum adsorption concentration temperature of 30 DEG C. for 2 hours, wherein an adsorbent for vacuum adsorption concentration is active carbon or nonpolar macroporous resin, which weighs twice as much as the original component A, and then obtaining a concentrated solution A;

the step V of infrared-microwave drying comprises:
Step (8) performing hot air-infrared-microwave drying on the obtained concentrated solution A in a drying cavity, wherein the hot air temperature is 40 DEG C., the far infrared radiation intensity is 0.5 W/cm<2>, the power in the first stage of microwave heating is 300 W, the power in the second stage is 400 W, and the power in the third stage is 500 W, a speed of a conveying belt is 5 m/min, and the drying operation is cyclically performed for 3 times; and drying the concentrated solution A under an infrared and microwave environment till the moisture content is less than 4 percent, thus obtaining a component A dry powder;

the step VI of packaging and sterilization of a finished product:
Step (9) adding the obtained component A dry powder, a component B, a component C and a residual component D into a stirrer according to raw material ratios, mixing the raw materials, stirring the raw materials in the stirrer at a rotating speed of 1,500 r/min for 25 minutes, then stopping the stirrer, homogenizing the raw materials, controlling the temperature of the material solution at 40 DEG C. and the homogenization pressure at 10 MPa during homogenization, performing metering and bagging, and performing pasteurization for 10 minutes, thus obtaining a finished product.

Wherein soybean processing includes: selecting sun-cured and full high-quality soybeans which have a golden yellow color and are free of pest damage, washing the soybeans with water, weighing the soybeans according to a raw weight of the amount, putting the soybeans into a pan for frying till the soybeans are cooked, and grinding the soybeans into powder of 200 meshes; soybeans for the soybean isolate protein powder are processed by: baking the soybeans at 80 DEG C. for 20 minutes, soaking the soybeans in a NaHCO$_3$ solution at the mass percent concentration of 2 percent for 120 seconds, quickly freezing the soybeans at −20 DEG C. for 5 minutes, and drying the soybeans at 50 DEG C. with hot air for 110 minutes.

Embodiment 4

A preparation method of a Chinese meal package is provided, including:
Step I, pretreatment of raw materials;
Step II, drying;
Step III, freeze grinding;
Step IV, filtering through a biological ceramic film;
Step V, infrared-microwave drying;
Step VI, packaging and sterilizing a finished product.

Wherein the step I of pretreatment of the raw materials specifically includes:

Step (1) weighing the raw material components according to ratios, cleaning a component A to remove impurities, sterilizing the component A in a far infrared sterilizer for 25 seconds, then performing high temperature sterilization under the set conditions of a sterilization temperature range of 90 DEG C., a pressure at 10 MPa and a sterilization time length range of 13 minutes;

Step (2) soaking the sterilized component A in milk for 24 hours till the milk content is 25 weight percent;

the step II of drying specifically includes:

Step (3) drying the milk-soaked component A in a vacuum microwave dryer at a drying temperature of 35 DEG C. for 8 minutes, and controlling the vacuum degree at 8 KPa and the microwave power at 400 W, thus obtaining a dried component A;

Step (4) freezing the component A dried in the step (3) at −20 DEG C. for 4 hours for freezing treatment, then taking out the component A, putting the component A into a vacuum freeze dryer, firstly freezing the component A at a cooling speed of 10 DEG C./min till the temperature of the component A is −35 DEG C., maintaining the temperature for 4 hours, then putting the component A into a freezer at a temperature of −30 DEG C. for constant temperature freezing for 3 hours, thus obtaining a freeze-dried component A;

the step III of freeze grinding specifically includes:

Step (5) grinding the freeze-dried component A in an ultrafine cell wall breaking grinder into powder of 400 meshes, adding deionized water in an amount twice that of the component A powder, into the ground component A powder, and then treating the component A powder with an ultrasonic continuous flow cell crushing machine at an ultrasonic frequency of 30 KHz, power of 1,500 W and the flow of suspension per hour of 10 Kg, thus obtaining crushed component A powder suspension for later use;

the step IV of filtering with the biological ceramic film specifically includes:

Step (6) filtering the component A powder suspension: filtering the component A powder suspension with the microfiltration biological ceramic film, respectively collecting interceptions and filtrate, and then continuously filtering the filtrate with an ultrafiltration film, thus obtaining ultrafiltration film filtrate A for later use, wherein the microfiltration film is an alumina-based nano inorganic film with a molecular weight cut-off of 1,000 MW and the microfiltration temperature is 35 DEG C.; the ultrafiltration film has a molecular weight cut-off of 300 MW and the ultrafiltration temperature is 40 DEG C.; the nano inorganic film has a thickness of 15 microns, and is prepared from the following raw materials in part by weight: 20 parts of silicon nitride, 5 parts of zinc oxide, 3 parts of yttria stabilized zirconia, 15 parts of titanium carbide, 8 parts of glass fiber, 5 parts of aluminum oxide and 3 parts of magnesium oxide;

Step (7) concentrating the material solution A by a vacuum adsorption method at a vacuum adsorption concentration temperature of 40 DEG C. for 4 hours, wherein an adsorbent for vacuum adsorption concentration is active carbon or nonpolar macroporous resin, which weighs twice as much as the original component A, and then obtaining a concentrated solution A;

the step V of infrared-microwave drying comprises:

Step (8) performing hot air-infrared-microwave drying on the obtained concentrated solution A in a drying cavity, wherein the hot air temperature is 45 DEG C., the far infrared radiation intensity is 0.8 W/cm<2>, the power in the first stage of microwave heating is 400 W, the power in the second stage is 500 W, and the power in the third stage is 400 W, a speed of a conveying belt is 10 m/min, and the drying operation is cyclically performed for 4 times; and drying the concentrated solution A under an infrared and microwave environment till the moisture content is less than 4 percent, thus obtaining a component A dry powder;

the step VI of packaging and sterilization of a finished product:

Step (9) adding the obtained component A dry powder, a component B, a component C and a residual component D into a stirrer according to raw material ratios, mixing the raw materials, stirring the raw materials in the stirrer at a rotating speed of 1,500 r/min for 35 minutes, then stopping the stirrer, homogenizing the raw materials, controlling the temperature of the material solution at 50 DEG C. and the homogenization pressure at 15 MPa during homogenization, performing metering and bagging, and performing pasteurization for 15 minutes, thus obtaining a finished product.

Wherein soybean processing includes: selecting sun-cured and full high-quality soybeans which have a golden yellow color and are free of pest damage, washing the soybeans with water, weighing the soybeans according to a raw weight of the amount, putting the soybeans into a pan for frying till the soybeans are cooked, and grinding the soybeans into powder of 200 meshes; soybeans for the soybean isolate protein powder are processed by: baking the soybeans at 100 DEG C. for 30 minutes, soaking the soybeans in a NaHCO$_3$ solution at the mass percent concentration of 3 percent for 150 seconds, quickly freezing the soybeans at −20 DEG C. for 10 minutes, and drying the soybeans at 60 DEG C. with hot air for 150 minutes.

Mr. Zhao, who is 68 years old, male and suffering from hyperhidrosis and insomnia, started to take the product of the disclosure respectively in the morning and evening, 30 grams for each time. After he insisted on taking the product for 90 days, his sleep quality was improved, the hyperhidrosis was cured, and the diet became regular.

Mr. Wang, who is 45 years old, male, obese and suffering from fatty liver, took the product of the disclosure respectively in the morning and evening every day, 30 grams for each time. After he insisted on taking the product for 90 days, the weight was reduced by 3 kilograms, and the fatty liver was cured.

Mrs. Li, who is 72 years old, female and suffering from cataract, took the product of the disclosure in the morning and evening every day, 30 grams for each time. After she insisted on taking the product for 90 days, the eyesight was improved, and she felt good in food taste.

In the end, it should be noted that obviously, the above embodiments are only examples for a clear explanation of the disclosure, but not intended to limit implementation modes. An ordinary person skilled in the art further can make changes or variations in other different forms on the basis of the above explanation. No more examples need to be or can be made to all the implementation modes here, but the obvious changes or variations derived therefrom still fall within the scope of protection of the disclosure.

The invention claimed is:

1. A Chinese meal package, characterized by being prepared from the following raw materials in part by weight:
a component A, a component B, a component C and a component D according to a ratio of 1 to 1 to 1 to 1, wherein the component A is prepared from the following raw material components:
3,000 to 3,500 parts of an agaricus blazei extract
60,000 to 65,000 parts of yam
3,000 to 3,500 parts of phaseolus calcaratus
200 to 240 parts of glabridin
5,000 to 5,500 parts of a black bean peel extract
the component B is prepared from the following raw material components:
2,000 to 2,200 parts of total sugar
2,122.3 to 2,431.6 parts of mineral substances
20,000 to 25,000 parts of corn fiber powder
17,000 to 20,000 parts of inulin
60,000 to 65,000 parts of soybean isolate protein powder
500 to 520 parts of L-carnitine
200 to 220 parts of β carotene
100 to 120 parts of Q10 coenzyme
3,000 to 3,300 parts of lycopene
500 to 530 parts of a citrus extract
6,000 to 6,300 parts of a conifer cherry extract
600 to 650 parts of a grape seed extract
10,000 to 15,000 parts of lecithin
4,000 to 4,300 parts of a tremella extract
2,000 to 2,200 parts of a white hyacinth bean extract
4,000 to 4,300 parts of a semen coicis extract
2,000 to 2,300 parts of an okra extract
2,000 to 2,200 parts of a rose flower extract
the component C is prepared from the following raw material components:
32 to 38 parts of vitamin B1
32 to 41 parts of vitamin B2
32 to 45 parts of vitamin B6
0.032 to 0.02 parts of vitamin B12
360 to 400 parts of vitamin C
0.72 to 1 part of vitamin A
0.022 to 0.5 part of vitamin K
0.009 to 0.056 part of vitamin D
420 to 450 parts of vitamin E
0.032 to 0.56 parts of biotin
0.48 to 1 part of folic acid
32 to 55 parts of pantothenic acid
32 to 50 parts of nicotinic acid
the component D is prepared from the following raw material components:
550 to 650 parts of milk
80,000 to 90,000 parts of deionized water.

2. The Chinese meal package according to claim 1, characterized in that the mineral substances consist of the following raw material components in part by weight: 1,300 to 1,500 parts of calcium, 650 to 720 parts of magnesium, 21.6 to 35 parts of iron, 144 to 165 parts of zinc, 0.3 to 1 part of selenium, 0.3 to 0.9 part of chromium, 1.8 to 2.8 parts of copper, 3.6 to 5.6 parts of manganese and 0.7 to 1.3 parts of vanadium.

3. The Chinese meal package according to claim 1, characterized in that the total sugar is prepared from one of or a combination of several of sorbitol, xylooligosaccharide and sucralose.

4. The Chinese meal package according to claim 1, characterized in that the raw material components of the meal package and the weight parts are as follows:
the component A is prepared from the following raw material components:
3,000 parts of the agaricus blazei extract
60,000 parts of the yam
3,000 parts of the phaseolus calcaratus
200 parts of the glabridin
5,000 parts of the black bean peel extract
the component B is prepared from the following raw material components:
2,000 parts of the total sugar
1,300 parts of calcium
650 parts of magnesium
21.6 parts of iron
144 parts of zinc
0.3 part of selenium
0.3 part of chromium
1.8 parts of copper
3.6 parts of manganese
0.7 part of vanadium
20,000 parts of the corn fiber powder
17,000 parts of the inulin
60,000 parts of the soybean isolate protein powder
500 parts of the L-carnitine
200 parts of the β carotene
100 parts of the Q10 coenzyme
3,000 parts of the lycopene
500 parts of the citrus extract
6,000 parts of the conifer cherry extract
600 parts of the grape seed extract
10,000 parts of the lecithin
4,000 parts of the tremella extract
2,000 parts of the white hyacinth bean extract
4,000 parts of the semen coicis extract
2,000 parts of the okra extract
2,000 parts of the rose flower extract
the component C is prepared from the following raw material components:
32 parts of the vitamin B1
32 parts of the vitamin B2
32 parts of the vitamin B6
0.032 parts of the vitamin B12
360 parts of the vitamin C
0.72 part of the vitamin A
0.022 part of the vitamin K
0.009 part of the vitamin D
420 parts of the vitamin E
0.032 parts of the biotin
0.48 part of the folic acid
32 part of the pantothenic acid
32 part of the nicotinic acid
the component D is prepared from the following raw material components:
550 parts of the milk
80,000 parts of the deionized water.

5. The Chinese meal package according to claim 1, characterized in that the raw material components of the meal package and the weight parts are as follows:
the component A is prepared from the following raw material components:
3,500 parts of the agaricus blazei extract
65,000 parts of the yam
3,500 parts of the phaseolus calcaratus
240 parts of the glabridin
5,500 parts of the black bean peel extract the component B is prepared from the following raw material components:
2,200 parts of the total sugar
2,431.6 parts of the mineral substances
25,000 parts of the corn fiber powder
20,000 parts of the inulin
65,000 parts of the soybean isolate protein powder
520 parts of the L-carnitine
220 parts of the β carotene
120 parts of the Q10 coenzyme
3,300 parts of the lycopene
530 parts of the citrus extract
6,300 parts of the conifer cherry extract
650 parts of the grape seed extract
15,000 parts of the lecithin
4,300 parts of the tremella extract
2,200 parts of the white hyacinth bean extract
4,300 parts of the semen coicis extract
2,300 parts of the okra extract
2,200 parts of the rose flower extract
the component C is prepared from the following raw material components:
38 parts of the vitamin B1
41 parts of the vitamin B2
45 parts of the vitamin B6
0.02 parts of the vitamin B12
400 parts of the vitamin C
1 part of the vitamin A
0.5 part of the vitamin K
0.056 part of the vitamin D
450 parts of the vitamin E
0.56 parts of the biotin
1 part of the folic acid
55 part of the pantothenic acid
50 part of the nicotinic acid
the component D is prepared from the following raw material components:
650 parts of the milk
90,000 parts of the deionized water;
wherein the mineral substances consist of the following raw material components in part by weight: 1,500 parts of calcium, 720 parts of magnesium, 35 parts of iron, 165 parts of zinc, 1 part of selenium, 0.9 part of chromium, 2.8 parts of copper, 5.6 parts of manganese and 1.3 parts of vanadium.

6. The Chinese meal package according to claim 1, characterized in that the meal package provides energy of 800 to 850 Kcal/day/person and 90 to 95 percent of high-quality protein.

7. A preparation method of the Chinese meal package according to claim 1, characterized by comprising:
Step I, pretreatment of raw materials;
Step II, drying;
Step III, freeze grinding;
Step IV, filtering with a biological ceramic film;
Step V, infrared-microwave drying;
Step VI, packaging and sterilization of a finished product.

8. The method of the Chinese meal package according to claim 7, characterized in that the step I of pretreatment of the raw materials specifically comprises:
Step (1) weighing the raw material components according to ratios, cleaning a component A to remove impurities, sterilizing the component A in a far infrared sterilizer for 20 to 25 seconds, then performing high temperature sterilization under the set conditions of a sterilization temperature range between 80 and 90 DEG C., a pressure between 8 and 10 MPa and a sterilization time length range between 8 and 13 minutes;
Step (2) soaking the sterilized component A in milk for 1 to 24 hours till the milk content is 20 to 25 weight percent;
the step II of drying specifically comprises:
Step (3) drying the milk-soaked component A in a vacuum microwave dryer at a drying temperature of 30 to 35 DEG C. for 5 to 8 minutes, and controlling the vacuum degree at 5 to 8 KPa and the microwave power at 200 to 400 W, thus obtaining a dried component A;
Step (4) freezing the component A dried in the step (3) at −15 to −20 DEG C. for 2 to 4 hours for freezing treatment, then taking out the component A, putting the component A into a vacuum freeze dryer, firstly freezing the component A at a cooling speed of 5 to 10 DEG C./min till the temperature of the component A is −25 to −35 DEG C., maintaining the temperature for 2 to 4 hours, then putting the component A into a freezer at a temperature of −25 to −30 DEG C. for constant temperature freezing for 3 hours, thus obtaining a freeze-dried component A;
the step III of freeze grinding specifically comprises:
Step (5) grinding the freeze-dried component A in an ultrafine cell wall breaking grinder into powder of 400 meshes, adding deionized water in an amount twice that of the component A powder into the ground component A powder, and then treating the component A powder with an ultrasonic continuous flow cell crushing machine at an ultrasonic frequency of 15 to 30 KHz, power of 1,000 to 1,500 W and the flow of suspension per hour of 10 Kg, thus obtaining crushed component A powder suspension for later use;
the step IV of filtering with the biological ceramic film specifically comprises:
Step (6) filtering the component A powder suspension: filtering the component A powder suspension with the microfiltration biological ceramic film, respectively collecting interceptions and filtrate, and then continuously filtering the filtrate with an ultrafiltration film, thus obtaining ultrafiltration film filtrate A for later use, wherein the microfiltration film is an alumina-based nano inorganic film with a molecular weight cut-off of 1,000 MW and the microfiltration temperature is 30 to 35 DEG C.; the ultrafiltration film has a molecular weight cut-off of 300 MW and the ultrafiltration temperature is 40 DEG C.; the nano inorganic film has a thickness of 10 to 15 microns, and is prepared from the following raw materials in part by weight: 15 to 20 parts of silicon nitride, 1 to 5 parts of zinc oxide, 2 to 3 parts of yttria stabilized zirconia, 10 to 15 parts of titanium carbide, 5 to 8 parts of glass fiber, 3 to 5 parts of aluminum oxide and 1 to 3 parts of magnesium oxide;
Step (7) concentrating the material solution A by a vacuum adsorption method at a vacuum adsorption concentration temperature of 30 to 40 DEG C. for 2 to 4 hours, wherein an adsorbent for vacuum adsorption concentration is active carbon or nonpolar macroporous resin, of which the weight is 1-2 times that of the original component A, and then obtaining a concentrated solution A;
the step V of infrared-microwave drying comprises:
Step (8) performing hot air-infrared-microwave drying on the obtained concentrated solution A in a drying cavity, wherein the hot air temperature is 40 to 45 DEG C., the far infrared radiation intensity is 0.5 to 0.8 W/cm<2>, the power in the first stage of microwave heating is 300 to 400 W, the power in the second stage is 400 to 500 W, and the power in the third stage is 500 to 400 W, a speed of a conveying belt is 5 to 10 m/min, and the drying operation is cyclically performed for 3 to 4 times; and drying the concentrated solution A under an infrared and microwave environment till the moisture content is less than 4 percent, thus obtaining a component A dry powder;

the step VI of packaging and sterilization of a finished product:

Step (9) adding the obtained component A dry powder, a component B, a component C and a residual component D into a stirrer according to raw material ratios, mixing the raw materials, stirring the raw materials in the stirrer at a rotating speed of 1,500 r/min for 25 to 35 minutes, then stopping the stirrer, homogenizing the raw materials, controlling the temperature of the material solution at 40 to 50 DEG C. and the homogenization pressure at 10 to 15 MPa during homogenization, performing metering and bagging, and performing pasteurization for 10 to 15 minutes, thus obtaining a finished product.

9. The method of the Chinese meal package according to claim 8, characterized in that soybean processing comprises: selecting sun-cured and full high-quality soybeans which have a golden yellow color and are free of pest damage, washing the soybeans with water, weighing the soybeans according to a raw weight of the amount, putting the soybeans into a pan for frying till the soybeans are cooked, and grinding the soybeans into powder of 200 meshes; soybeans for the soybean isolate protein powder are processed by: baking the soybeans at 80 to 100 DEG C. for 20 to 30 minutes, soaking the soybeans in a $NaHCO_3$ solution at the mass percent concentration of 2 to 3 percent for 120 to 150 seconds, quickly freezing the soybeans at −20 DEG C. for 5 to 10 minutes, and drying the soybeans at 50 to 60 DEG C. with hot air for 110 to 150 minutes.

* * * * *